(12) United States Patent
Kounnas et al.

(10) Patent No.: US 8,871,460 B2
(45) Date of Patent: Oct. 28, 2014

(54) GAMMA-SECRETASE MODULATORY COMPOUNDS, METHODS FOR IDENTIFYING SAME, AND USES THEREFOR

(75) Inventors: Maria Z. Kounnas, San Diego, CA (US); Elizabeth J. Ackermann, Del Mar, CA (US); Kenneth A. Stauderman, San Diego, CA (US); Gonul Velicelebi, San Diego, CA (US); Steve Wagner, San Diego, CA (US)

(73) Assignee: Neurogenetic Pharmaceuticals, Inc., Del Mar, CA (US)

( * ) Notice: Subject to any disclaimer, the term of this patent is extended or adjusted under 35 U.S.C. 154(b) by 0 days.

(21) Appl. No.: 13/508,511

(22) PCT Filed: Nov. 8, 2010

(86) PCT No.: PCT/US2010/055869
§ 371 (c)(1),
(2), (4) Date: Aug. 1, 2012

(87) PCT Pub. No.: WO2011/057214
PCT Pub. Date: May 12, 2011

(65) Prior Publication Data
US 2012/0289558 A1    Nov. 15, 2012

Related U.S. Application Data

(60) Provisional application No. 61/259,570, filed on Nov. 9, 2009.

(51) Int. Cl.
*C12Q 1/37* (2006.01)
*G01N 33/68* (2006.01)

(52) U.S. Cl.
CPC ........ *G01N 33/6896* (2013.01); *G01N 2500/02* (2013.01)
USPC .............................................. 435/23; 435/24

(58) Field of Classification Search
CPC ............................................ G01N 2800/2821
USPC .................................................... 435/23, 24
See application file for complete search history.

(56) References Cited

U.S. PATENT DOCUMENTS

| | | |
|---|---|---|
| 3,710,795 A | 1/1973 | Higuchi et al. |
| RE28,819 E | 5/1976 | Thompson |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,522,811 A | 6/1985 | Eppstein et al. |
| 5,672,805 A | 9/1997 | Neve |
| 5,811,633 A | 9/1998 | Wadsworth et al. |
| 5,877,399 A | 3/1999 | Hsiao et al. |
| 2005/0070538 A1 | 3/2005 | Cheng et al. |
| 2009/0105345 A1* | 4/2009 | Ho ................................ 514/570 |

FOREIGN PATENT DOCUMENTS

| | | |
|---|---|---|
| EP | 1821103 A1 | 8/2007 |
| WO | WO 2004/018997 A2 | 3/2004 |
| WO | WO 2006/112550 A2 | 10/2006 |
| WO | WO 2007/092861 A2 | 8/2007 |

OTHER PUBLICATIONS

Beher et al. "Selected non-steroidal anti-inflammatory drugs and their derivatives target gamma-secretase at a novel site", JBC, 2004, 279(42):43419-43426.*
Chen et al., "Presenilin 1 Mutations Activate $\gamma_{42}$-Secretase but Reciprocally Inhibit ε-Secretase Cleavage of Amyloid Precursor Protein (APP) and S-3-Cleavage of Notch*", *The Journal of Biological Chemistry*, 277(39):36521-36526 (2002).
Crystal et al., "Membrane Topology of γ-Secretase Component PEN-2*", *The Journal of Biological Chemistry*, 278(22):20117-2012 (2003).
Czirr et al., "Independent Generation of Aβ42 and Aβ38 Peptide Species by 'γ-Secretase", *The Journal of Biological Chemistry*, 263(25):17049-17054 (2008).
Edbauer et al., "Reconstition of γ-secretase activity", *Nature Cell Biology*, 5:466-488 (2003).
Extended European Search Report dated Jul. 11, 2013 for European Application No. EP 108292467, 10 pages.

(Continued)

*Primary Examiner* — Bin Shen
(74) *Attorney, Agent, or Firm* — Kilpatrick Townsend & Stockton LLP

(57) ABSTRACT

In accordance with the present invention, it has been discovered that compounds which modulate the γ-secretase enzyme to make more of the shorter, less toxic and less aggregation-prone Aβ peptides (such as Aβ37 and Aβ38), while making less of the longer and more toxic and aggregation-prone AB peptides (such as AB40 and AB42) are useful as gamma-secretase modulators. In addition, these GSM compounds have further been discovered to have the selective property of modulating the formation of various AB peptides, while not inhibiting the overall activity of the γ-secretase enzyme. Thus, such compounds do not impede other critical functions of the γ-secretase enzyme, such as generating fragments from Notch that appear to control gene expression and cell differentiation. Therefore, in accordance with the present invention, there are provided screening assays useful for determining whether test compounds have GSM activity; accordingly, invention assays facilitate the identification of new gamma-secretase modulators. Such screening assays can be performed in a variety of ways, e.g., by assessing whether test compounds: lower the level of Aβ42 peptide, increase the level of Aβ37 and/or Aβ38 peptides, have substantially no effect on the processing of other γ-secretase substrates, and/or interact with at least one component of the γ-secretase complex. Also provided in accordance with the present invention are compounds having gamma-secretase modulatory activity as identified by any of the methods described herein; methods for producing formulations useful for modulating gamma-secretase activity, as well as the resulting formulations; methods for modulating gamma-secretase activity employing compounds identified according to invention methods and/or invention formulations, and the like.

10 Claims, 1 Drawing Sheet

(56) References Cited

OTHER PUBLICATIONS

Games et al., "Alzheimer-type neuropathology in transgenic mice overexpressing V717F β-amyloid precursor protein", *Nature*, 373:523-527 (1995).

Hayashi et al., "Selective Reconstitution and Recovery of Functional 65-Secretase Complex on Budded Baculovirus Particles*", *The Journal of Biological Chemistry*, 279(36)38040-38046 (2004).

Hsiao et al., "Correlative Memory Deficits, Aβ Elevation, and Amyloid Plaques in Transgenic Mice", *Science*, 274;99-102 (1996).

International Search Report dated Apr. 22, 2011 for International Application No. PCT/US2010/055869, 2 pages.

Kim and Sisodia, "A Sequence within the First Transmembrane Domain of PEN-2 Is Critical for PEN-2-mediated Endoproteolysis of Presenilin 1*", *The Journal of Biological Chemistry*, 280(3):1992-2001 (2005).

Lee et al., "Presenilin-dependent β-Secretase-like Intramembrane Cleavage of ErbB4*", *The Journal of Biological Chemistry*, 277(8):6318-6323 (2002).

Luo et al., "PEN-2 and APH-1 Coordinately Regulate Proteolytic Processing of Presenilin 1*", *The Journal of Biological Chemistry*, 273(10):7850-7854 (2003).

Marambaud et al., "A presenilin-1/γ-secretase cleavage releases the E-cadherin intracellular domain and regulates disassembly of adherens junctions", *The EMBO Journal*, 21(8):1948-1956 (2002).

Neve et al., "Transgenic Mice Expressing APP-C100 in the Brain", *Neurobiology of Aging*, 17(2)191-203 (1996).

Schroeter et al., "Notch-1 signalling requires ligand-ineduced proteolytic release of intracellular domain", *Nature*, 393:382-386 (1998).

Steiner et al., "PEN-2 is an Integral Component of the γ-Secretase Complex Required for Coordinated Expression of Presenilin and Nicastrin*", *The Journal of Biological Chemistry*, 277(42):39062-39065 (2002).

Tian et al., "Linear Non-competitive Inhibition of Solubilized Human γ-Secretase by Pepstatin A Methylester, L685458, Sulfonamides, and Benzodiazepines*", *The Journal of Biological Chemistry*, 277(35):31499-31505 (2002).

Wärnmark et al., "Differential Recruitment of the Mammalian Mediator Subunit TRAP220 by Estrogen Receptors ERα and ERβ", *The Journal of Biological Chemistry*, 276(26):23397-23404 (2001).

Weggen et al., "A subset of NSAIDS lower amyloidogenic Aβ42 independently of cyclooxygenase activity", *Nature*, 414:212-216 (2001).

Wiltfang et al., "Improved electrophoretic separation and immunoblotting of beta-amyloid (Aβ) peptides 1-40, 1-42, and 1-43", *Electrophoresis*, 18:527-532 (1997).

Xia and Wolfe, "Intramembrane proteolysis by presenilin and presenilin-like proteases", *Journal of Cell Science*, 116(14):2839-2844 (2003).

M. Kounnas et al., "Modulation of [gamma]-Secretase Reduces [beta Deposition in a Transgenic Mouse Model of Alzheimer's Disease", Neuron, vol. 67, No. 5, 2010, pp. 769-780.

Office Action dated Dec. 20, 2013 in EP10829246.7.

* cited by examiner

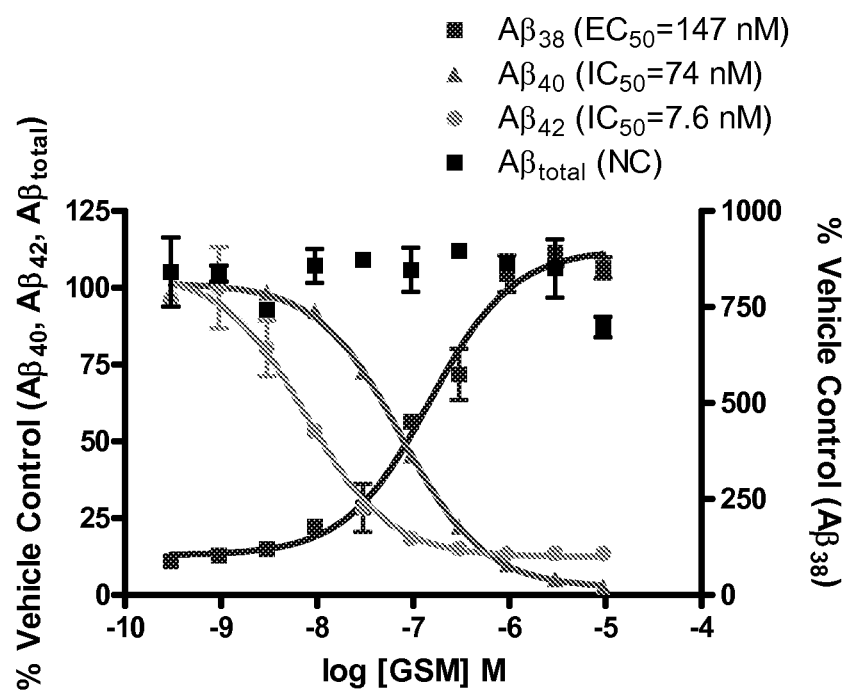

GAMMA-SECRETASE MODULATORY COMPOUNDS, METHODS FOR IDENTIFYING SAME, AND USES THEREFOR

RELATED APPLICATIONS

This application claims priority from international application no. PCT/US10/55869, filed Nov. 8, 2010, which in turn claims priority from U.S. provisional patent application No. 61/259,570, filed Nov. 9, 2009, the entire contents of each of which are hereby incorporated by reference herein.

FIELD OF THE INVENTION

The present invention relates to methods for determining whether test compounds have gamma-secretase modulatory activity. In a particular aspect, the present invention relates to compounds identified by invention methods, as well as for formulations containing same. In a further aspect, the invention relates to methods for modulating gamma-secretase activity employing compounds identified employing invention assay methods.

BACKGROUND OF THE INVENTION

A major pathological hallmark of Alzheimer's disease (AD) is the abundance of deposits, called neuritic plaques, in key areas of the brain that control memory and cognition. These neuritic plaques are largely comprised of aggregations of fibrillar peptides referred to as amyloid β (Aβ) peptides. The longest of these Aβ peptides, designated Aβ42, is the most prone to aggregate into plaques that ultimately interfere with the neuronal connectivity at synapses within the brain. Individuals genetically predisposed to early-onset forms of AD invariably make a greater proportion of the longer Aβ peptides, especially Aβ42, relative to unaffected individuals. Aβ peptides, including the pathogenic Aβ42 peptide, are derived via proteolysis from a much larger precursor molecule known as the amyloid β precursor protein (APP).

During normal catabolism, two crucial enzymes, or proteases, are responsible for generating these Aβ peptides from APP. The first enzyme, beta-secretase (β-secretase), cuts the APP molecule into two major pieces comprised of an extracellular fragment and a membrane-associated fragment. The second enzyme, gamma-secretase (γ-secretase), then cleaves the membrane-associated fragment into one of several different forms of Aβ peptide. Gamma-secretase is currently understood to be a membrane complex of at least four proteins: presenilin (PS-1 or PS-2), nicastrin, Aph-1, and Pen-2. Activation of γ-secretase requires that PS-1 is endoproteolyzed into two fragments, each of which is believed to contribute one aspartate to the active site of the aspartyl protease activity.

Substantial efforts have been devoted to developing drugs that lower Aβ peptide levels by inhibiting gamma-secretase activity. However, these gamma-secretase inhibitors (GSIs) have been associated with gastrointestinal side effects, probably because they interfere with other necessary functions of gamma-secretase such as Notch proteolytic processing (e.g., LY-450,139) resulting in goblet cell hyperplasia. Indeed, a number of these GSI's have been shown to directly interact with PS-1.

Recently, a series of gamma-secretase modulatory compounds have been identified that modulate the enzyme's activity towards APP without preventing it from performing its other normal functions (e.g., Notch proteolysis, E-cadherin proteolysis). These compounds, referred to as gamma-secretase modulators (GSMs), are predicted to overcome some of the pitfalls associated with the GSI compounds. As such, these GSMs may be improved therapeutics. These GSM's are distinct from the far less potent substrate binding, NSAID (non-steroidal anti-inflammatory drug)-like GSM's described by Weggen S. et al. "A subset of NSAIDS lower amyloidogenic $A\beta_{42}$ independently of cyclooxygenase activity" in Nature (2001) 414: 212-216.

However, the molecular target of gamma-secretase modulators is as yet unknown. Identification of the molecular target of GSMs would facilitate development of improved treatments for AD (and related indications) and provide approaches to screen for, and identify, new GSMs that can be used to prevent or treat AD and other diseases associated with pathogenic deposits of Aβ.

SUMMARY OF THE INVENTION

In accordance with the present invention, it has been discovered that compounds which modulate the γ-secretase enzyme to make more of the shorter, less toxic and less aggregation-prone Aβ peptides (such as Aβ37 and Aβ38), while making less of the longer and more toxic and aggregation-prone Aβ peptides (such as Aβ40 and Aβ42) are useful as gamma-secretase modulators. In addition, these GSM compounds have further been discovered to have the selective property of modulating the formation of various Aβ peptides, while not inhibiting the overall activity of the γ-secretase enzyme. Thus, such compounds do not impede other critical functions of the γ-secretase enzyme, such as generating fragments from Notch that appear to control gene expression and cell differentiation.

Therefore, in accordance with the present invention, there are provided screening assays useful for determining whether test compounds have GSM activity; accordingly, invention assays facilitate the identification of new gamma-secretase modulators. Such screening assays can be performed in a variety of ways, e.g., by assessing whether test compounds:
  lower the level of Aβ40 and/or Aβ42 peptides,
  increase the level of Aβ37 and/or Aβ38 peptides,
  have substantially no effect on the processing of other γ-secretase substrates, and/or
  interact with at least one component of the γ-secretase complex.

Also provided in accordance with the present invention are compounds having gamma-secretase modulatory activity as identified by any of the methods described herein; methods for producing formulations useful for modulating gamma-secretase activity, as well as the resulting formulations; methods for modulating gamma-secretase activity employing compounds identified according to invention methods and/or invention formulations, and the like.

BRIEF DESCRIPTION OF THE FIGURE

FIG. 1 summarizes the effect of an exemplary gamma secretase modulator (GSM) according to the invention on various Aβ alloforms. In the FIGURE, Aβ38 is indicated by blue boxes, Aβ40 is indicated by triangles, Aβ42 is indicated by circles, and Aβ total is indicated by black boxes.

DETAILED DESCRIPTION OF THE INVENTION

In accordance with the present invention, there are provided screening methods for determining whether a test compound has gamma-secretase modulatory activity. Invention methods comprise:

determining whether said test compound:
  lowers the level of Aβ42 peptide,
  increases the level of Aβ37 and/or Aβ38 peptides,
  has substantially no effect on the processing of other γ-secretase substrates, and
  interacts with at least one component of the γ-secretase complex;
wherein compounds which meet each of the above criteria are identified as having gamma-secretase modulatory activity.

In accordance with any of the preceding embodiments of the present invention, test compounds which have gamma-secretase modulatory activity may be further characterized as also lowering the level of Aβ40 peptide, but typically having less potent effects on lowering Aβ40 peptide relative to effects thereof on Aβ42.

In accordance with any of the preceding embodiments of the present invention, test compounds which have gamma-secretase modulatory activity may be further characterized as having substantially no effect on the processing of Notch, E-cadherin, and/or LRP, and/or the formation of AICD.

In accordance with any of the preceding embodiments of the present invention, the interaction of test compound with at least one component of the γ-secretase complex may comprise direct binding thereof to said at least one component of the γ-secretase complex. Alternatively, the interaction of test compound with at least one component of the γ-secretase complex may comprise indirect binding thereof to said at least one component of the γ-secretase complex.

In accordance with any of the preceding embodiments of the present invention, the at least one component of the γ-secretase complex with which test compounds having gamma-secretase modulatory activity interact may be selected from the group consisting of Presenilin, Pen-2, nicastrin, and Aph-1.

In accordance with another aspect of the present invention, there are provided screening methods for determining whether a test compound that interacts with at least one component of the γ-secretase complex has gamma-secretase modulatory activity, said method comprising:
  determining whether said test compound:
    lowers the level of Aβ42 peptide,
    increases the level of Aβ37 and/or Aβ38 peptides, and
    has substantially no effect on the processing of other γ-secretase substrates,
wherein compounds which interact with at least one component of the γ-secretase complex and meet each of the above criteria are identified as having gamma-secretase modulatory activity.

In accordance with any of the preceding embodiments of the present invention, test compounds which have gamma-secretase modulatory activity may be further characterized as also lowering the level of Aβ40 peptide, but typically having less potent effects on lowering Aβ40 peptide relative to effects thereof on Aβ42.

In accordance with any of the preceding embodiments of the present invention, test compounds which have gamma-secretase modulatory activity may be further characterized as having substantially no effect on the processing of Notch, E-cadherin, and/or LRP, and/or the formation of AICD.

In accordance with any of the preceding embodiments of the present invention, the interaction of test compound with at least one component of the γ-secretase complex may comprise direct binding thereof to said at least one component of the γ-secretase complex. Alternatively, the interaction of test compound with at least one component of the γ-secretase complex may comprise indirect binding thereof to said at least one component of the γ-secretase complex.

In accordance with any of the preceding embodiments of the present invention, the at least one component of the γ-secretase complex with which test compounds having gamma-secretase modulatory activity interact may be selected from the group consisting of Presenilin, Pen-2, nicastrin, and Aph-1.

In accordance with still another aspect of the present invention, there are provided screening methods for determining whether a test compound that interacts with at least one component of the γ-secretase complex, yet has substantially no effect on the processing of γ-secretase substrates other than Aβ37, Aβ38, Aβ40 and/or Aβ42 peptides, has gamma-secretase modulatory activity, said method comprising:
  determining whether said test compound:
    lowers the level of Aβ42 peptide, and
    increases the level of Aβ37 and/or Aβ38 peptides,
  wherein compounds which interacts with at least one component of the γ-secretase complex, yet have substantially no effect on the processing of other γ-secretase substrates, and meet each of the above criteria are identified as having gamma-secretase modulatory activity.

In accordance with any of the preceding embodiments of the present invention, test compounds which have gamma-secretase modulatory activity may be further characterized as also lowering the level of Aβ40 peptide, but typically having less potent effects on lowering Aβ40 peptide relative to effects thereof on Aβ42.

In accordance with any of the preceding embodiments of the present invention, test compounds which have gamma-secretase modulatory activity may be further characterized as having substantially no effect on the processing of Notch, E-cadherin, and/or LRP, and/or the formation of AICD.

In accordance with any of the preceding embodiments of the present invention, the interaction of test compound with at least one component of the γ-secretase complex may comprise direct binding thereof to said at least one component of the γ-secretase complex. Alternatively, the interaction of test compound with at least one component of the γ-secretase complex may comprise indirect binding thereof to said at least one component of the γ-secretase complex.

In accordance with any of the preceding embodiments of the present invention, the at least one component of the γ-secretase complex with which test compounds having gamma-secretase modulatory activity interact may be selected from the group consisting of Presenilin, Pen-2, nicastrin, and Aph-1.

In accordance with yet another aspect of the present invention, there are provided screening methods for determining whether a test compound that lowers the level of Aβ42 peptide, yet has substantially no effect on the processing of γ-secretase substrates other than Aβ37, Aβ38, Aβ40 and/or Aβ42 peptides, has gamma-secretase modulatory activity, said method comprising:
  determining whether said test compound:
    increases the level of Aβ37 and/or Aβ38 peptides, and
    interacts with at least one component of the γ-secretase complex,
wherein compounds which meet each of the above criteria are identified as having gamma-secretase modulatory activity.

In accordance with any of the preceding embodiments of the present invention, test compounds which have gamma-secretase modulatory activity may be further characterized as also lowering the level of Aβ40 peptide, but typically having less potent effects on lowering Aβ40 peptide relative to effects thereof on Aβ42.

In accordance with any of the preceding embodiments of the present invention, test compounds which have gamma-secretase modulatory activity may be further characterized as having substantially no effect on the processing of Notch, E-cadherin, and/or LRP, and/or the formation of AICD.

In accordance with any of the preceding embodiments of the present invention, the interaction of test compound with at least one component of the γ-secretase complex may comprise direct binding thereof to said at least one component of the γ-secretase complex. Alternatively, the interaction of test compound with at least one component of the γ-secretase complex may comprise indirect binding thereof to said at least one component of the γ-secretase complex.

In accordance with any of the preceding embodiments of the present invention, the at least one component of the γ-secretase complex with which test compounds having gamma-secretase modulatory activity interact may be selected from the group consisting of Presenilin, Pen-2, nicastrin, and Aph-1.

In accordance with a still further aspect of the present invention, there are provided methods for determining whether a test compound that lowers the level of Aβ42 peptide and interacts with at least one component of the γ-secretase complex has gamma-secretase modulatory activity, said method comprising:
determining whether said test compound:
increases the level of Aβ37 and/or Aβ38 peptides, and
has substantially no effect on the processing of other γ-secretase substrates,
wherein compounds which lower the level of Aβ42 peptide, interacts with at least one component of the γ-secretase complex, and meet each of the above criteria are identified as having gamma-secretase modulatory activity.

In accordance with any of the preceding embodiments of the present invention, test compounds which have gamma-secretase modulatory activity may be further characterized as also lowering the level of Aβ40 peptide, but typically having less potent effects on lowering Aβ40 peptide relative to effects thereof on Aβ42.

In accordance with any of the preceding embodiments of the present invention, test compounds which have gamma-secretase modulatory activity may be further characterized as having substantially no effect on the processing of Notch, E-cadherin, and/or LRP, and/or the formation of AICD.

In accordance with any of the preceding embodiments of the present invention, the interaction of test compound with at least one component of the γ-secretase complex may comprise direct binding thereof to said at least one component of the γ-secretase complex. Alternatively, the interaction of test compound with at least one component of the γ-secretase complex may comprise indirect binding thereof to said at least one component of the γ-secretase complex.

In accordance with any of the preceding embodiments of the present invention, the at least one component of the γ-secretase complex with which test compounds having gamma-secretase modulatory activity interact may be selected from the group consisting of Presenilin, Pen-2, nicastrin, and Aph-1.

In accordance with another aspect of the present invention, there are provided methods for the determining whether a test compound that interacts with at least one component of the γ-secretase complex, lowers the level of Aβ42 peptide, and has substantially no effect on the processing of γ-secretase substrates other than Aβ37, Aβ38, Aβ40 and/or Aβ42 peptides, has gamma-secretase modulatory activity, said method comprising determining whether said test compound increases the level of Aβ37 and/or Aβ38 peptides, wherein compounds which meet the above criteria are identified as having gamma-secretase modulatory activity.

The above-described methods allow one to distinguish those compounds which modulate gamma-secretase activity from those compounds which inhibit gamma-secretase activity.

Also provided in accordance with the present invention are compounds having gamma-secretase modulatory activity identified by any of the above-described methods.

Exemplary gamma-secretase modulators contemplated for use herein include compounds having a structure corresponding to Formula (I):

$$(A-L_A)_{0-1}-(B)-L_B-(C)-L_C-(D) \quad (I)$$

and pharmaceutically acceptable salts, and prodrugs thereof, wherein:
A is optional, and when present is a five or six-membered substituted or unsubstituted cycloalkyl, heterocyclyl, aryl, heteroaryl, cycloalkylene, heterocyclylene, arylene, or heteroarylene;
B is a five or six-membered substituted or unsubstituted cycloalkylene, heterocyclylene, arylene, or heteroarylene; or $B_1$, together with $A_1$, forms a fused ring system;
C is a five or six-membered substituted or unsubstituted arylene or heteroarylene;
D is a five or six-membered substituted or unsubstituted aryl, heteroaryl, arylene, or heteroarylene;
$L_A$ is optional, and when present, is a covalent bond or a linker; and
each of $L_B$ and $L_C$ is independently a covalent bond or a linker.

Presently preferred gamma-secretase modulators contemplated for use herein include compounds having a structure corresponding to Formula (II):

$$(A_1)-(B_1)-(C_1)-L_{C1}-(D_1) \quad (II)$$

and pharmaceutically acceptable salts, and prodrugs thereof, wherein:
$A_1$ is an optionally substituted 1,3-imidazole or a 1,2,3-triazole;
$B_1$ is an optionally substituted phenyl or pyridyl;
$C_1$ is an optionally substituted thiazole;
$D_1$ is a substituted aryl; and
$L_{C1}$ is an amino linker linked at the 2-position of the thiazole,
wherein said compound has gamma-secretase modulatory activity.

In certain embodiments of the present invention, $A_1$ is an optionally substituted 1,3-imidazole. A presently preferred imidazole contemplated herein is a methyl-substituted 1,3-imidazole, with 4-methyl 1,3-imidazole being presently preferred.

In certain embodiments of the present invention, $B_1$ is an optionally substituted phenyl. Exemplary optionally substituted phenyls include fluoro- or methoxy-substituted phenyl.

In certain embodiments of the present invention, $B_1$ is an optionally substituted pyridyl.

In certain embodiments of the present invention, $C_1$ is a thiazole.

In certain embodiments of the present invention, $D_1$ is a di- or tri-alkyl substituted phenyl. Exemplary di- or tri-alkyl substituted phenyls include 2,4-dimethyl-5-ethyl phenyl or 2-methyl-4-methoxy-5-isopropyl phenyl.

Compounds of particular interest herein, having been shown to meet each of the criteria set forth above to qualify as a gamma-secretase modulator (as opposed to a gamma-secretase inhibitor), include compounds wherein:

A₁ is 4-methyl 1,3-imidazole;
B₁ is 2-fluoro phenyl;
C₁ is thiazole;
D₁ is 2-methyl, 4-(2-aminoethoxy) 5-isopropyl phenyl; and
L_{C1} is —NH— linked at the 2-position of the thiazole (Compound 1), or
compounds wherein:
A₁ is 4-methyl 1,3-imidazole;
B₁ is 2-fluoro phenyl;
C₁ is thiazole;
D₁ is 2-methyl, 4-methoxy, 5-isopropyl phenyl; and
L_{C1} is —NH— linked at the 2-position of the thiazole (Compound 2),
as well as compounds having the structure:

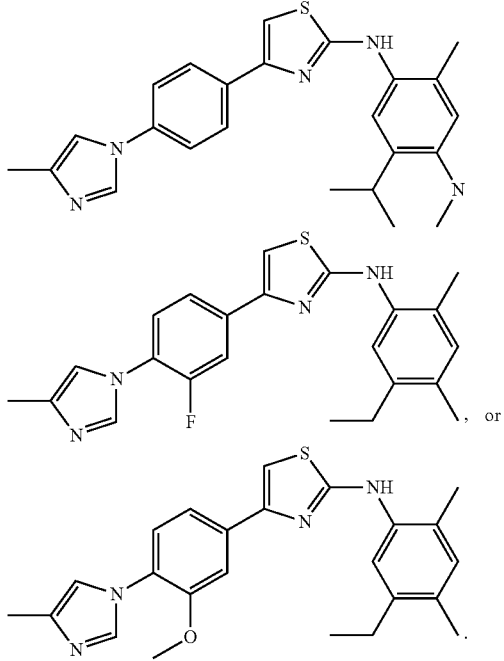

Also provided in accordance with the present invention are methods for producing formulations useful for modulating gamma-secretase activity. Invention methods comprise formulating compounds identified as having gamma-secretase modulatory activity by any of the above-described methods in a pharmaceutically acceptable carrier therefor.

Also provided in accordance with the present invention are formulations produced by the above-described method.

The phrase "pharmaceutically acceptable carrier" refers to any carrier known to those skilled in the art to be suitable for the particular mode of administration. In addition, the compounds identified by any of the above-described methods may be formulated as the sole pharmaceutically active ingredient in the composition or may be combined with other active ingredients.

The phrase "pharmaceutically acceptable salt" refers to any salt preparation that is appropriate for use in a pharmaceutical application. Pharmaceutically-acceptable salts include amine salts, such as N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine, tris(hydroxymethyl)aminomethane, and the like; alkali metal salts, such as lithium, potassium, sodium, and the like; alkali earth metal salts, such as barium, calcium, magnesium, and the like; transition metal salts, such as zinc, aluminum, and the like; other metal salts, such as sodium hydrogen phosphate, disodium phosphate, and the like; mineral acids, such as hydrochlorides, sulfates, and the like; and salts of organic acids, such as acetates, lactates, malates, tartrates, citrates, ascorbates, succinates, butyrates, valerates, fumarates, and the like.

The phrase "prodrug" refers to a compound that, upon in vivo administration, is metabolized by one or more steps or processes or otherwise converted to the biologically, pharmaceutically or therapeutically active form of the compound. Prodrugs can be prepared by modifying functional groups present in the compound in such a way that the modifications are cleaved, either in routine manipulation or in vivo, to a compound described herein. For example, prodrugs include compounds of the present invention wherein a hydroxy, amino, or sulfhydryl group is bonded to any group that, when administered to a mammalian subject, can be cleaved to form a free hydroxyl, free amino, or free sulfhydryl group, respectively. Representative prodrugs include, for example, esters, enol ethers, enol esters, acetates, formates, benzoate derivatives, and the like of alcohol and amine functional groups in the compounds of the present invention. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

Compositions herein comprise one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders to be treated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in PCT publication WO 04/018997, and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

In one embodiment, a therapeutically effective dosage should produce a serum concentration of active ingredient of from about 0.1 ng/ml to about 50-100 µg/ml. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% (wt %) with the balance made up from non-toxic carrier may be prepared. Methods for preparation of these compositions are known to those skilled in the art. The contemplated compositions may contain 0.001%-100% (wt %) active ingredient, in one embodiment 0.1-95% (wt %), in another embodiment 75-85% (wt %).

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a Sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial Sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a Sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, Sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, Sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial Sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044, 126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% (vol %) isotonic solutions, pH about 5-7, with appropriate salts.

Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Combination Therapy

In another embodiment, the compounds may be administered in combination, or sequentially, with another therapeutic agent. Such other therapeutic agents include those known for treatment, prevention, or amelioration of one or more symptoms of amyloidosis and neurodegenerative diseases and disorders. Such therapeutic agents include, but are not limited to, donepezil hydrochloride (Aracept), rivastigmine tartrate (Exelon), tacrine hydrochloride (Cognex) and galantamine hydrobromide (Reminyl).

Also provided in accordance with the present invention are methods for modulating gamma-secretase activity. Invention methods comprise administering an effective amount of a compound identified by any of the methods described herein to a subject in need thereof.

Also provided in accordance with the present invention are methods for modulating gamma-secretase activity by administering an effective amount of an invention formulation to a subject in need thereof.

Components of the γ-Secretase Complex

Presenilin

Presenilins are a family of related multi-pass transmembrane proteins that function as a part of the gamma-secretase protease complex. Vertebrates have two presenilin genes, called PSEN1 (located on chromosome 14 in humans) that encodes presenilin 1 (PS-1) and PSEN2 (on chromosome 1 in humans) that codes for presenilin 2 (PS-2). Both genes show conservation between species, with little difference between rat and human presenilins.

Presenilins undergo cleavage in an alpha helical region of one of the cytoplasmic loops to produce a larger N-terminal and a smaller C-terminal fragment which together form part of the functional protein. Cleavage of presenilin 1 can be prevented by a mutation which causes the loss of exon 9, and results in loss of function. Presenilins play a key role in the modulation of intracellular $Ca^{2+}$ involved in presynaptic neurotransmitter release and long-term potentiation induction.

Pen-2 Protein

Presenilin Enhancer Polypeptide 2 (Pen-2) is a component of the gamma-secretase enzyme complex, along with presenilin (PS1 or PS2), nicastrin, and Aph-1. As used herein, the term "Pen-2" refers to a protein having substantially the amino acid sequence of a native Pen-2 protein, and at least one Pen-2 functional activity. Such a protein can have either a native Pen-2 sequence, or a modified Pen-2 sequence.

Native Pen-2 amino acid sequences include, for example, mammalian Pen-2, such as human Pen-2 (GenBank Accession NP_758844), bovine Pen-2 (GenBank Accession AAV84001), and mouse Pen-2 (GenBank Accession NP_079774); non-mammalian vertebrate Pen-2, such as zebrafish Pen-2 (GenBank Accession NP_991139); and invertebrate Pen-2, such as mosquito Pen-2 (GenBank Accession XP_317362), *C. elegans* Pen-2 (GenBank Accession NP_499459), and *Drosophila* Pen-2 (GenBank Accession NP_788401).

A modified Pen-2 amino acid sequence can include one or more additions, deletions or substitutions with respect to a native sequence. In particular, a modification can include a conservative substitution, such as substitution of an apolar amino acid with another apolar amino acid (such as replacement of leucine with isoleucine), or substitution of a charged amino acid with a similarly charged amino acid (such as replacement of a glutamic acid with an aspartic acid). A modification can also include a nonconservative change, wherein a substituted amino acid has different but sufficiently similar structural or chemical properties that permits such a substitution without adversely affecting the desired functional activity. Exemplary Pen-2 proteins that retain functional activity while having amino acid substitutions are described in Kim and Sisodia (2005) J. Biol. Chem. 280: 1992-2001.

A modified Pen-2 sequence can also include one or more chemical or enzymatic modifications, including but not limited to replacement of hydrogen by an alkyl, acyl, or amino group; esterification of a carboxyl group with a suitable alkyl or aryl moiety; alkylation of a hydroxyl group to form an ether derivative; phosphorylation or dephosphorylation of a serine, threonine or tyrosine residue; or N- or O-linked glycosylation.

A modified Pen-2 sequence can also be a fragment of Pen-2. Exemplary human Pen-2 fragments have been described in Kim and Sisodia (2005) supra. Pen-2 fragments can contain all or part of the N-terminal domain (approximately residues 1-17), the first transmembrane domain (approximately residues 18-38), the cytoplasmic domain (approximately residues 39-60), the second transmembrane domain (approximately residues 61-78), and/or the C-terminal domain (approximately residues 79-101). Pen-2 fragments optionally may lack regions shown to be dispensable for promoting presenilin 1 (PS1) endoproteolysis or gamma-secretase activity, such as residues 3-9, 40-46, 85-92, or 93-100, and likewise may contain regions shown to be important for stability or membrane insertion (approximately residues 10-16 and 52-60), binding to PS1, Nicastrin and/or Aph1 (approximately residues 18-36), promoting endoproteolysis of PS1 and gamma-secretase activity (approximately residues 18-31), or for stabilizing the proteolyzed PS1 dimer (approximately residues 85-101).

Those skilled in the art can determine suitable modified forms of Pen-2 for a given application. For example, Pen-2 can be modified to facilitate its purification, or to increase its stability, solubility, or activity in a particular assay. Addition of tag sequences, such as epitope tags, histidine tags, glutathione-S-transferase (GST), detectable labels (e.g. radiolabels, biotin, enzymes, and the like), or addition of sorting sequences, can facilitate purification, retention, or detection of the protein.

Depending on the desired modification and the source of the protein, the modification can be introduced into the Pen-2 protein, or into its encoding nucleic acid sequence, by methods known in the art (see, for example, Kim and Sisodia (2005) supra, and Crystal et al. (2003) J. Biol. Chem. 278: 20117-20123 (2003)).

A non-native Pen-2 protein can be tested by methods known in the art and described herein to confirm that it retains at least one Pen-2 functional activity.

Pen-2 Functional Activity

As described above, a Pen-2 protein useful in certain invention screening assays has Pen-2 functional activity. Additionally, certain invention screening assays contemplate determining whether a test compound modulates Pen-2 functional activity. As used herein, the term "Pen-2 functional activity" refers to the exhibition of one or more of the following properties:

a) the ability to bind to gamma-secretase components, including nicastrin, presenilin 1 and/or presenilin 2;

b) the ability to reconstitute gamma-secretase activity in association with presenilin, nicastrin and Aph-1;

c) the ability to promote presenilin endoproteolysis and/or stabilize presenilin proteolytic fragments in association with presenilin, nicastrin and Aph-1; and d) the ability to bind to a predetermined gamma secretase modulator.

Binding of Pen-2 to gamma-secretase components can be assessed, for example, by co-immunoprecipitation using endogenously or recombinantly expressed Pen-2 with endogenous or recombinantly expressed gamma-secretase components. Suitable reagents (e.g. antibodies that recognize Pen-2, PS1s, and Nct; constructs; cell lines, etc.) and methods for performing such assays, are known in the art (see Steiner et al. (2002) J. Biol. Chem. 277:39062-39065). Alternative methods of assessing protein-protein interactions, using either in vitro or cell-based assays, are known in the art and can be modified for use in the invention screening assays. Such methods include, for example, two-hybrid techniques, protein fragment complementation, resonance energy transfer, tandem affinity purification (TAP), protein chip arrays, isothermal titration calorimetry, surface plasmon resonance (SPR) and related solid phase techniques, mass specroscopy, and single molecule techniques such as atomic force microscopy and fluorescence correlation spectroscopy (reviewed in Piehler (2005) Curr. Opin. Structural Biol. 15:4-14). A suitable method can be chosen based on the desire to identify the Pen-2 binding partner, to determine the binding affinity, and/ or to determine the binding kinetics.

The ability of Pen-2 to reconstitute gamma-secretase activity, or to promote presenilin endoproteolysis or stabilization of presenilin proteolytic fragments, in association with other gamma-secretase components, can be assessed in any suitable system. For example, these functional activities can be assessed in a reconstituted baculovirus (e.g. Hayashi et al. (2004) J. Biol. Chem. 279:38040-38046), yeast (e.g. Edbauer et al. (2003) Nature Cell Biol. 5:486-488), or mammalian system (e.g. Kim and Sisodia (2005) supra). Reconstituted gamma-secretase activity can be assessed by determining the effect of Pen-2 on cleavage of any gamma-secretase substrate, such as APP, Notch, E-cadherin, Erb-B4, CD44, LRP and Nectin 1α. Promotion of presenilin endoproteolysis or stabilization of presenilin fragments can be assessed by determining the levels of presenilin holoprotein or of N-terminal or C-terminal derivatives (see Kim and Sisodia (2005) supra).

Another functional activity of Pen-2 is the ability to bind to a predetermined gamma-secretase modulator, such as compounds determined by the methods described herein to have gamma-secretase modulatory activity, and other known GSM compounds discussed below.

Compounds can be tested for their ability to modulate one or more of these Pen-2 functional activities. As used herein, the term "modulates" with respect to Pen-2 functional activity refers to a change, preferably a statistically significant change, in a Pen-2 functional activity in the presence of a suitable concentration (e.g. sub-nanomolar to sub-millimolar) of the test compound but not in the presence of a vehicle control (or in the absence of the test compound). Specificity of the effect of the test compound on Pen-2 functional activity can be further assessed by determining whether the test compound also modulates a functional activity of a different protein, such as a functional activity of another gamma-secretase component or of an irrelevant protein.

Pen-2 Binding Assays

Certain invention screening assays contemplate determining whether a compound binds Pen-2. As used herein, a compound that "binds Pen-2" binds with substantially higher affinity to a Pen-2 protein than to an unrelated protein, such as glutathione-S transferase or bovine serum albumin. Depending on the assay, the affinity of the compound for binding Pen-2 can be greater than about $10^{-4}$ M, including greater than about $10^{-5}$ M, such as greater than about $10^{-6}$ M, greater than about $10^{-7}$ M, or greater than about $10^{-8}$ M. The corresponding affinity for the unrelated protein can be at least 2-fold less, such as at least 5-fold, 10-fold, 50-fold or 100-fold less.

Methods of determining the binding of a compound to a protein are known in the art, and include both competitive and direct binding assays. Depending on the application of the method and the number of compounds being assessed, binding assays may either be high-throughput or low-throughput.

1) Competitive Binding Assays:

As readily recognized by those of skill in the art, competitive binding assays can be carried out in a variety of ways to identify compounds that bind Pen-2. Such assays generally will involve a source of Pen-2 (which can be isolated or in a mixture with other cell components), a detectably labeled compound that is known to bind Pen-2, and an unlabeled test compound, although other combinations are contemplated. The Pen-2 can optionally be attached to a solid surface, such as a multi-well plate, resin, bead, or membrane. Such attachment can be effected directly, such as by adsorption, or via a linker or antibody. If the source of Pen-2 is cells expressing or overexpressing Pen-2, the cells can be plated on the surface of a culture plate and allowed to attach. The Pen-2 can also be present in a cell extract (such as a membrane preparation from cells expressing or overexpressing Pen-2) or other non-solid medium (e.g. an in vitro lysate, liposome, suspension, or solution). The binding compound, if labeled, can have attached, covalently or non-covalently, a detectable moiety, such as a fluorescent, luminescent, or radioactive (e.g. $^{125}I$, $^{14}C$ or $^{3}H$) moiety to facilitate the ability to quantify.

Generally, in a competitive binding assay, an amount of Pen-2 is incubated with one or more test compounds in the presence of a given amount of a detectably labeled compound known to bind Pen-2 (which optionally is pre-bound to Pen-2), under suitable conditions (e.g. buffers, detergents, time, temperature, wash conditions) and test compounds are identified that cause a reduction in the amount of detectable label specifically associated with Pen-2. When such assays are performed in a cell extract, solution or other non-solid medium, the Pen-2 can subsequently be retained on a solid surface, such as a resin bound to anti-Pen-2 antibodies or a filter, or passed through a column, or precipitated, in order to distinguish the amount of detectable label associated with Pen-2 (i.e. the amount of bound compound) from that which is free.

Depending on the nature of the assay, suitable control assays can be performed. For example, controls for assays involving surface-bound Pen-2 can include surfaces coated with irrelevant proteins, whereas controls for assays involving cells or cell extracts can include cells or extracts from cells with different levels of Pen-2 expression (e.g. cells from Pen-2 knockout animals, or cells expressing higher levels of Pen-2).

2) Direct Binding Assays:

As readily recognized by those of skill in the art, direct binding assays can be carried out in a variety of ways to identify compounds that bind Pen-2, e.g., by coating a surface (e.g. a multi-well plate, addressable bead, resin, etc.) with test compound(s), incubating the coated surface with detectably labeled Pen-2 protein, and identifying a compound that causes retention of label on the surface (or variations thereof, such as incubating with unlabeled Pen-2 followed by incubating with a detectably labeled antibody to Pen-2). For instance, described herein are direct binding assays in which a test compound is attached to an Affi-Gel resin, the resin is incubated with either cell lysate containing unlabeled Pen-2 (Example 1) or with isolated unlabeled Pen-2 (Example 2), resin-bound Pen-2 is separated from free Pen-2 by washing followed by detergent elution, and the amount of resin-bound Pen-2 determined by immunoblotting with anti-Pen-2 antibodies.

Alternatively, such assays can be carried out by coating a surface with isolated Pen-2 protein, incubating the coated surface with detectably labeled test compounds, and identifying a compound that causes retention of label on the surface.

As yet another alternative, such assays can be carried out by incubating a Pen-2 protein with test compounds in a surface plasmon resonance system (e.g. a Biacore sensor chip) and identifying a compound that causes a change in surface plasmon resonance, as described in Example 3.

As still another alternative, such assays can be carried out by incubating a Pen-2 protein that undergoes a change in a detectable physical property (e.g. increase or decrease in Fluorescence Resonance Energy Transfer (FRET) or Bioluminescence Resonance Energy Transfer (BRET)) upon compound binding with test compounds, and identifying a compound that causes the detectable change.

Alternative methods of determining the binding between a compound and a protein are known in the art, and can be modified to assess binding to Pen-2. Such methods can involve Scintillation Proximity Assays (SPA), Amplified Luminescent Proximity Homogeneous Assay (AlphaScreen™), isothermal titration calorimetry, differential scanning calorimetry, gel electrophoresis, NMR spectroscopy, chromatography (including gel filtration), and the like.

Nicastrin

Nicastrin (abbreviated NCT) is a protein that is part of the gamma-secretase protein complex, which is one of the proteases involved in processing amyloid precursor protein (APP) to the short Alzheimer's disease-associated peptide amyloid beta. The other proteins in the complex are presenilin, which is the catalytically active component of the complex, APH-1 (anterior pharynx-defective 1), and PEN-2 (presenilin enhancer 2). Nicastrin itself is not catalytically active, but instead promotes the maturation and proper trafficking of the other proteins in the complex, all of which undergo significant post-translational modification before becoming active in the cell. Nicastrin has also been identified as a regulator of neprilysin, an enzyme involved in the degradation of amyloid beta fragment.

Aph-1

APH-1 (anterior pharynx-defective 1) is a protein gene product originally identified in the Notch signaling pathway in *Caenorhabditis elegans* as a regulator of the cell-surface localization of nicastrin. APH-1 homologs in other organisms, including humans, have since been identified as components of the gamma-secretase complex along with the catalytic subunit presenilin and the regulatory subunits nicastrin and PEN-2. The gamma-secretase complex is a multimeric protease responsible for the intramembrane proteolysis of transmembrane proteins such as the Notch protein and amyloid precursor protein (APP). Gamma-secretase cleavage of APP is one of two proteolytic steps required to generate the peptide known as amyloid beta, whose misfolded form is implicated in the causation of Alzheimer's disease. All of the components of the gamma-secretase complex undergo extensive post-translational modification, especially proteolytic activation; APH-1 and PEN-2 are regarded as regulators of the maturation process of the catalytic component presenilin. APH-1 contains a conserved alpha helix interaction motif glycine-X-X-X-glycine (GXXXG) that is essential to both assembly of the gamma secretase complex and to the maturation of the components.

Gamma-Secretase Modulatory Activity

Invention assays contemplate determining whether a compound has gamma-secretase modulatory activity. As used herein, the term "gamma-secretase modulatory activity" refers to the exhibition of one or more of the following properties in a suitable in vitro or in vivo assay:

a) the ability to raise the level of Aβ37, at a suitable concentration (e.g. sub-nanomolar to sub-millimolar);

b) the ability to raise the level of Aβ38, at a suitable concentration (e.g. sub-nanomolar to sub-millimolar);

c) the ability to lower the level of Aβ40 and/or Aβ42 without substantially inhibiting ε-cleavage of a γ-secretase substrate; and d) the ability to lower the level of Aβ40 and/or Aβ42 without substantially lowering total Aβ.

A compound with GSM activity thus can be distinguished from a compound with gamma-secretase inhibitory activity, which typically would lower the levels of Aβ37 and Aβ38 peptides (as well as Aβ40 and Aβ42), lower total Aβ, and inhibit ε-cleavage of γ-secretase substrates.

A compound that has the ability to modulate gamma-secretase activity is useful for a variety of applications, especially for the treatment of diseases associated with aberrant Aβ levels, and for prophylaxis of individuals susceptible to development of such diseases, as described further below.

Amyloid Beta Assays

As used herein, the term "amyloid beta" or "Aβ" refers to any peptide that corresponds in sequence to a peptide derived from both beta-secretase (BACE) and gamma-secretase cleavage of an amyloid precursor protein (APP).

As used herein, the terms "Aβ37," "Aβ38," "Aβ40" and "Aβ42" refer specifically to those Aβ peptides that terminate at positions 37, 38, 40 and 42, respectively, relative to human Aβ1-42 (SEQ ID NO:1; Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala) or Aβ1-42 homologs from other species. Since BACE is able to cleave APP at multiple sites (including between residues 671 and 672, between residues 672 and 673, and between residues 681 and 682, relative to the human APP770 sequence, GenBank Accession No. PO$_{5067}$) the N-terminus of an Aβ37, Aβ38, Aβ40 or Aβ42 peptide may vary. Thus, for example, the term Aβ37 includes peptides corresponding to amino acids 1-37, 2-37, and 11-37 of SEQ ID NO:1 or its homologs; likewise, Aβ38 includes peptides corresponding to amino acids 1-38, 2-38, and 11-38 of SEQ ID NO:1 or its homologs; Aβ40 includes peptides corresponding to amino acids 1-40, 2-40, and 11-40 of SEQ ID NO:1 or its homologs; and Aβ42 includes peptides corresponding to amino acids 1-42, 2-42, and 11-42 of SEQ ID NO:1 or its homologs.

As used herein, the term "total Aβ" refers to the sum total of all forms of Aβ, including Aβ33, Aβ34, Aβ37, Aβ38, Aβ40, Aβ42 and Aβ43. However, depending on the antibody or antibodies used in the assay, the forms of Aβ that can be detected in an assay for total Aβ may include only Aβ peptides which have the epitope of interest (e.g. residues 1-x for antibodies raised against the N-terminus).

As used herein, the terms "raise the level" or "lower the level" of an Aβ peptide or of total Aβ refers to a statistically significant change in the amount of an Aβ peptide or total Aβ in a suitable cell-based or in vivo assay upon exposure to a compound. In general, in a cell-based assay, the level of Aβ secreted into the extracellular medium is determined, although in certain assays the level of intracellular Aβ may additionally or alternatively be determined. Depending on the nature of the assay, the levels of soluble Aβ (which may be monomeric or oligomeric), or insoluble (fibrillar) Aβ, or both, is determined.

As used herein, the phrase "lower the level of Aβ40 and/or Aβ42 without substantially lowering total Aβ" means that the compound exhibits a separation in $IC_{50}$ of at least about 10-fold, such as about 50-fold, 100-fold, 200-fold or greater, between its inhibition of Aβ40 and/or Aβ42 and its inhibition of total Aβ. Expressed another way, at a concentration of compound that produces about 50% lowering of Aβ40 and/or Aβ42, little (less than about 10%) or no inhibition of total Aβ should be produced.

As readily recognized by those of skill in the art, various assays can be performed to determine whether a compound raises or lowers Aβ peptide levels. For most applications, the compound will be tested over a suitable range of concentrations, and a compound that raises or lowers the amount of Aβ will be determined to do so in a concentration-dependent manner, such that an $EC_{50}$ or $IC_{50}$ can be determined.

An assay to detect whether a compound raises or lowers Aβ peptide levels will involve a source of amyloid precursor protein (APP). The APP can be from any species, but is preferably human or mammalian, and can be any isoform, including the major isoforms APP695, APP751 and APP770, or other isoforms such as APP714, L-APP752, L-APP733, L-APP696, L-APP677, APP563, and APP365. The APP can contain one or more additions, deletions or mutations, including mutations found in families with AD or other amyloidoses (e.g. the Swedish (Lys670Asn, Met671Leu) double mutation; the London mutation (Val717Ile), the Indiana mutation (Val717Leu), the Val717Phe mutation, the Val717Gly mutation, the Ala713Thr mutation, the Ala713Val mutation, the Austrian mutation (Thr714Ile), the Iranian mutation (Thr714Ala), the French mutation (Val715Met), the German mutation (Val715Ala), the Florida mutation (Ile716Val), the Ile 716'Thr mutation, the Australian mutation (Leu723Pro), the Flemish mutation (Ala692Gly), the Dutch mutation (Glu693Gln), the Arctic mutation (Glu693Gly), the Italian mutation (Glu693Lys), the Iowa mutation (Asp694Asn), and the amyloidsis-Dutch type mutation (Glu693Gln); all numbering is given relative to the APP770 form).

Alternatively, an assay can use just a portion of an APP, so long as the fragment can be processed to Aβ by one or more cleavage reactions. For example, the APP C-terminal fragments designated C99 and C89, or portions thereof lacking some or all C-terminal residues that normally reside in the cytosol, can be used.

Depending on the desired assay, the source of APP or cleavable fragment can be an in vivo, ex vivo or in vitro substance. For example, a source of APP or cleavable fragment can be a live organism (including a human patient, or a veterinary or laboratory animal, such as a transgenic animal), a sample therefrom (such as a tissue (e.g. brain), body fluid (e.g. blood, plasma, cerebrospinal fluid, urine, etc.), or extract thereof), a cell (such as a primary cell or cell line, a recombinant cell, or extract thereof), extracellular medium or purified protein. Methods of isolating tissues, production and maintenance of primary and recombinant cells, preparation of lysates, and protein purification compatible with Aβ assays are known in the art.

For cell based Aβ assays, cells (including human or other mammalian cells) that endogenously or recombinantly express APP can be used, such as CHO-APP$_{Swe}$ (see Examples herein), HEK-APP$^{751}$, primary cells (e.g. mixed brain cultures) obtained from APP-expressing animals, and the like.

For in vivo Aβ assays, animals that endogenously express APP can be used, such as mice, rats, guinea pigs, rabbits, and the like. Alternatively, APP-expressing transgenic animals can be used, including but not limited to the Tg2576 mouse, which contains human APP695 with a gene encoding the Swedish (Lys670Asn, Met671Leu) double mutation under the control of the hamster prion protein gene promoter (Hsiao et al. (1996) Science 274:99-102; U.S. Pat. No. 5,877,399); the V717F PDAPP mouse, which contains a gene encoding human APP695 (Val717Phe) under the control of the platelet derived growth factor (PDGF) chain gene promoter (Games et al. (1995) Nature 373:523-527; U.S. Pat. No. 5,811,633); and the C100 mouse, which contains a gene encoding the neurotoxic C-terminal 100 amino acids of APP under the control of the dystrophin neural promoter (Neve et al. (1996) Neurobiol. Aging 17:191-203; U.S. Pat. No. 5,672,805).

In the Aβ assays contemplated herein, the substance containing the APP or cleavable fragment is contacted with a compound. As will be appreciated by one skilled in the art, when the substance is a human or other animal, the contacting can be by therapeutic or prophylactic administration of the compound (e.g. by oral, intravenous, intraperitoneal, etc. routes). When the substance is a tissue, tissue extract or cell, the contacting can be by introduction of the compound into the culture medium. When the substance is a cell lysate or a solution, the contacting can be by mixing the compound with the lysate or solution.

It will be appreciated that there are various assay formats available to detect the ability of a compound to raise or lower the level of Aβ. Assays using a sandwich ELISA format to detect changes in the level of Aβ40, Aβ42 and total Aβ, or an ultra-sensitive sandwich ELISA format to detect changes in the level of Aβ38, are described herein in Example 4. An assay using FRET to detect changes in the level of Aβ42 is described in US Published Application 2005/0070538. An assay using mass spectroscopy to detect changes in the level of (at least) Aβ37, Aβ38 and Aβ40 is described herein in Example 4. Likewise, an assay using electrophoresis and immunoblotting to detect changes in the level of Aβ37, Aβ38, Aβ40 and Aβ42 is described in Example 4. Alternative Aβ assays, and methods of modifying the exemplary Aβ assays described herein, are known in the art.

Epsilon-Cleavage Assays

Cleavage of APP within the transmembrane domain by gamma-secretase (preceded by BACE cleavage) generates the C-terminus of the various forms of Aβ peptide. This cleavage has been termed "γ cleavage". Analysis of the C-terminal stable counterpart fragments of gamma-secretase cleavage, i.e. those containing the cytoplasmic tail of APP (also called the "APP intracellular domain" or AICD), reveals that a second gamma-secretase cleavage event occurs (termed "ε cleavage") several residues C-terminal of the γ cleavage site, just within the cytoplasmic membrane boundary (Chen et al. (2002) J. Biol. Chem. 277:36521-36526).

Gamma-secretase modulatory compounds are characterized by not substantially inhibiting ε-cleavage of γ-secretase substrates. As used herein, the term "ε-cleavage" refers to cleavage of a gamma-secretase substrate, by gamma-secretase, at a site that is approximately the same position relative to the cytoplasmic membrane boundary as the ε-cleavage site on APP. Proteins that undergo ε-cleavage include, for example, APP, Notch, E-cadherin, Erb-B4, CD44, LRP, Nectin 1α, and the like, to generate fragments AICD, NICD, E-cad/CTF2, B4-ICD, CD44-ICD, LRP-ICD and NE-ICD, respectively (see Xia et al. (2003) J. Cell Science 116:2839-2844).

As used herein, the phrase "lower the level of Aβ40 and/or Aβ42 without substantially inhibiting ε-cleavage" means that the compound exhibits a separation in $IC_{50}$ of at least about 10-fold, such as about 50-fold, 100-fold, 200-fold or greater, between its inhibition of the cleavage that generates Aβ40 and/or Aβ42 and its inhibition of ε-cleavage. Expressed another way, at a concentration of compound that produces about 50% lowering of Aβ40 and/or Aβ42, little (less than about 10%) or no inhibition of ε-cleavage should be produced.

Various assays for assessing ε-cleavage activity are known in the art. For example, an assay to detect ε-cleavage of a recombinantly expressed Notch fragment is described herein in Example 4, and an assay for ε-cleavage of recombinantly expressed Erb-B4 is described in Lee et al. (2002) 277: 6318-6323.

An exemplary assay for ε-cleavage of endogenous E-cadherin is described in Marambaud et al. (2002) EMBO 21: 1948-1956. Either apoptosis or $Ca^{2+}$ influx induces the cleavage of full-length E-cadherin to produce three fragments, CTF1, CTF2 and CTF3, which can be detected using standard SDS-protein gel electrophoresis and western blotting with a C-terminal specific antibody. Gamma-secretase inhibitors, such as L-685,458, DAPT or Compound E, inhibit the formation of CTF2, while having no effect on CTF1 or CTF3. Gamma-secretase modulators, in contrast, do not substantially affect ε-cleavage activity, and no substantial inhibition of the formation of CTF2 is seen. In an exemplary assay, A431 cells, which endogenously express detectable levels of E-cadherin, are treated overnight with test compounds (or, as a positive control, with a gamma-secretase inhibitor) followed by treatment with staurosporine, and cell lysates are analyzed for levels of E-cad/CTF2 by western blotting.

Assays to determine ε-cleavage of other γ-secretase substrates are known in the art, and can likewise be used to assess or confirm gamma-secretase modulatory activity of a compound.

Therapeutic Applications

The invention contemplates administration of the above-described compounds and pharmaceutical compositions to subjects. As used herein, the term "subject" includes humans, as well as laboratory animals (e.g. transgenic mice expressing human APP), veterinary animals, and animals of commercial interest, e.g., bovine, ovine, and the like. Specifically contemplated is administration to subjects in need of modulation of gamma-secretase activity, such a subject having, or at risk of developing, a condition associated with aberrant Aβ levels. Such a condition can be characterized by an abnormal amount of at least one species of Aβ peptide (such as an increased level of Aβ42 or Aβ40, or a decreased level of Aβ37 or Aβ38); by an abnormal relative amount of different species of Aβ peptides (such as the ratio of Aβ42 to Aβ40); by an abnormal amount, or relative amount, of Aβ in a particular form (such as monomeric, oligomeric, or fibrillar form; in solution or aggregated in a plaque; in a particular conformation, etc.); and/or by an abnormal amount, or relative amount, of Aβ in a particular location (such as intracellular, membrane-associated or extracellular location, or in a particular tissue or body fluid).

Diseases and disorders characterized by aberrant Aβ levels are known in the art, and include, for example, Alzheimer's disease, Down syndrome, Parkinson's disease, diffuse Lewy body disease, progressive supranuclear palsy, multi-infarct dementia, dementia pugilistica, Hereditary Cerebral Hemorrhage with Amyloidosis-Dutch Type (HCHWA-D), cerebral amyloid angiopathy (CAA), and mild cognitive impairment (MCI). Compounds of the present invention can be administered to a subject to treat (including to prevent or to ameliorate) conditions associated with altered Aβ production, fibril formation/deposition, degradation and/or clearance, or any altered isoform of Aβ.

Compounds and compositions of the present invention can be used in the treatment of neurological disorders, including but not limited to neurodegenerative conditions and other dementias or traumatic conditions. Exemplary neurological disorders may include Pick's disease, multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, prion diseases (including Creutzfeldt-Jakob, Gerstmann-Straussler-Scheinker disease, Kuru and fatal familial insomnia), age-related dementia and other conditions with memory loss, such as vascular dementia, diffuse white matter disease (Binswanger's disease), dementia of endocrine or metabolic origin, dementia of head trauma and diffuse brain damage, dementia pugilistica and frontal lobe dementia, cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

Compounds and compositions of the instant invention may be used to treat or ameliorate a variety of other disorders. Compounds and compositions that may be used in therapeutic applications, in one embodiment have reasonably high bioavailability in a target tissue (i.e. brain, for neurodegenerative disorders; particular peripheral organs for other amyloidogenic conditions), and reasonably low toxicity. Those skilled in the art can assess compounds and compositions described herein for their pharmaceutical acceptability using standard methods.

For instance, compounds and compositions of the instant invention can be used in the treatment of cancer or other diseases characterized by abnormal cellular proliferation, inflammatory disease, bacterial or viral infection, autoimmune disease, acute pain, muscle pain, neuropathic pain, allergies, neurological disease, dermatological conditions, cardiovascular disease, diabetes, gastrointestinal disorders, depression, endocrine or other disease characterized by abnormal hormonal metabolism, obesity, osteoporosis or other bone disorders, pancreatic disease, epilepsy or seizure disorders, erectile or sexual dysfunction, opthamological disorders or diseases of the eye, cholesterol imbalance, hypertension or hypotension, migraine or headaches, obsessive compulsive disorder, panic disorder, anxiety disorder, post traumatic stress disorder, chemical dependency or addiction, and the like.

Compounds and compositions provided herein can also be used to prevent or treat amyloidoses. Amyloidoses include all conditions in which deposition of amyloid in the brain or periphery is a characteristic, including amyloidosis associated with rheumatic diseases, idiopathic diseases, inherited conditions, inflammatory conditions, infectious diseases and malignancies. Amyloidosis disorders include, for example, conditions associated with altered Aβ levels described above (e.g. Alzheimer's disease, Down syndrome, HCHWA-D, cerebral amyloid angiopathy (CAA), and mild cognitive impairment (MCI) etc.), as well as familial amyloid polyneuropathy, familial amyloid cardiomyopathy (Danish type), isolated cardiac amyloid, amyloid angiopathy, systemic senile amyloidosis, familial systemic amyloidosis, light-chain amyloidosis (AL), dialysis-associated amyloidosis, renal amyloidosis, prion-related encephalopathies, diabetes (in which amylin may be deposited in the kidney or pancreas), atrial amyloidosis and pituitary amyloidosis.

Those skilled in the art can determine other diseases and disorders for which administration of a compound or composition described herein can be beneficial.

The invention will now be described in greater detail with reference to the following non-limiting examples.

EXAMPLES

Example 1

This example shows that a gamma-secretase modulator, Compound 1 (i.e., a compound of Formula II, wherein:
$A_1$ is 4-methyl 1,3-imidazole;
$B_1$ is 2-fluoro phenyl;
$C_1$ is thiazole;
$D_1$ is 2-methyl-4-(2-aminoethoxy) 5-isopropyl phenyl; and
$L_{C1}$ is —NH— linked at the 2-position of the thiazole), selectively binds Pen-2 present in whole-cell lysates.

Compound 1, which bears a primary amine, was conjugated to Affi-Gel 10 resin (BioRad #153-6046) according to manufacturer's instructions. Compound 1 was dissolved in DMSO to a final concentration of 15 mg/ml. One ml of compound was mixed with approximately 1 ml of resin previously equilibrated in isopropanol. The compound and resin were rotated at room temperature for approximately 3 hr, washed with DMSO and the remaining unreacted groups were blocked with ethanolamine. The efficiency of coupling was generally greater than 80%, as determined by LC-MS analysis, with approximately 10-15 µmol of compound per ml of resin final concentration.

Solubilized whole-cell lysates from CHO-APP$_{Swe}$ cells (Chinese Hamster Ovary cells expressing human APP$^{695}$ with the K670N/M671L "Swedish" mutation) were prepared in PLC buffer (20 mM Hepes pH 7.5, 1 mM EDTA, 150 mM NaCl, 1% Triton X-100, 0.2% Tween-20). Lysates were precleared by incubating with 200 µl of blocked resin at 4° C. for 1 hr. The resin was pelleted and the resulting lysate was centrifuged at 13,000×g for 15 min to pellet any protein precipitates. One mg (approximately 2 mg/ml) of the precleared whole cell lysate was incubated with 100 µl of either Compound 1-conjugated resin, or with unconjugated resin, for two hours at room temperature, with constant rotation. After incubation, the resin was pelleted at low speed and the supernatant (i.e. unbound proteins) collected. The resin was washed 3-5 times with 1 ml of PLC buffer. Bound proteins were eluted with 200-300 µl aliquots of SDS denaturing sample buffer (0.25 M Tris-HCl, pH 6.8; 5% (w/v) SDS; 0.05% bromophenol blue; 10% glycerol; 2.5% 2-mercaptoethanol). Equal volumes of whole cell lysate (WCL) and supernatant in SDS denaturing sample buffer, as well as eluates from each resin, were run in separate lanes on a 4-20% SDS-PAGE gel. The electrophoresed proteins were transferred to a nitrocellulose membrane (Invitrogen #LC2001) and immunoblotted with antibodies that specifically recognize either Pen-2 (PNT2; gift of Gopal Thinakaran, see Luo et al. (2003), J. Biol. Chem. 278:7850-7854), presenilin 1 N-terminal fragment (PS1-NTF; gift of Gopal Thinakaran), presenilin 1 C-terminal fragment (PS1-CTF; Calbiochem #529592), nicastrin (Nct; Sigma #N-1660), amyloid precursor protein (APP; antibody R8666, PCT publication WO 04/018997) or phopholipase C-gamma (PLCγ; Upstate #06-152).

Pen-2 was observed to be present in the SDS eluate from the Compound 1-conjugated resin, but not from the unconjugated resin. Correspondingly, Pen-2 was substantially depleted from the whole cell lysate applied to the Compound 1-conjugated column. Although some amount of the N-terminal fragment (NTF) of PS1 also was present in the eluate, this fragment was not substantially depleted from the starting lysate, indicating minimal binding to Compound 1 and the possibility that this fragment instead directly bound to Pen-2. This possibility was supported by subsequent experiments, which demonstrated binding of Compound 1 to Pen-2 present in lysates prepared from PS1-deficient cells. APP holoenzyme (APP-Holo), the C-terminal fragment of PS1 (PS1-CTF), Nct, and PLCγ did not bind Compound 1-conjugated resin.

Example 2

This example shows that a gamma-secretase modulator, Compound 1, selectively binds isolated Pen-2 protein.

Prior to assessing binding to Compound 1, the proteins used in the binding assay were characterized. Purified GST (Abnova Corp) and GST-Pen2 (Abnova Corp #H00055851-PO1) proteins were confirmed to react with anti-GST (Novagen #71097-3) and anti-Pen-2 (PNT2) antibodies on an immunoblot. Additionally, the GST-Pen-2 protein, which contains a protease cleavage site between GST and Pen-2, was shown to be capable of cleavage using PreScission™ protease (Amersham #27-0843-01) to generate GST and Pen-2 proteins of the appropriate size (data not shown). To prepare purified Pen-2, about 1 µg of GST-Pen-2 was incubated with 4 µg of PreScission™ protease for 4 hr at 4° C. in Cleavage Buffer (50 mM Tris pH 7.4, 150 mM NaCl, 1 mM EDTA, 1% Triton X-100, 10% glycerol, 1 mg/ml phosphatidylcholine). Free GST and protease were removed by adding glutathione resin (Sigma #G4510) for 1 hr with rotation, and spinning down the resin. The supernatant, containing purified Pen-2, was collected.

Compound 1-conjugated and unconjugated Affi-Gel 10 resins were prepared essentially as described in Example 1. Purified Pen-2, GST-Pen-2 or GST proteins (0.2 to 0.6 µg were then incubated with 20 to 100 µl of either resin for 2 hr at room temperature in Cleavage Buffer containing 1 mM DTT ("start"). Following incubation, the resins were pelleted and the supernatants collected ("sup"). The resins were washed with ten times the bed volume of 20 mM Hepes pH 7.5 ("wash"), after which the bound proteins were eluted with 40 to 100 µl of denaturing sample buffer ("elute"). The proteins were electrophoresed through 4-20% SDS-PAGE gels, transferred to nitrocellulose membranes, and immunoblotted with either anti-GST or anti-Pen-2 antibodies.

Both Pen-2 and GST-Pen-2 were observed to selectively bind to the Compound 1-conjugated resin, as evidenced by the presence of an anti-Pen-2 reactive band in the "elute" lane from the Compound 1-conjugated resin but not from the unconjugated resin. In contrast, GST did not bind to the Compound 1 resin.

Example 3

This example shows the selective binding of a gamma-secretase modulator, Compound 2 (i.e., a compound of Formula II, wherein:
   $A_1$ is 4-methyl 1,3-imidazole;
   $B_1$ is 2-fluoro phenyl;
   $C_1$ is thiazole;
   $D_1$ is 2-methyl-4-methoxy-5-isopropyl phenyl; and
   $L_{C1}$ is —NH— linked at the 2-position of the thiazole),
but not a gamma-secretase inhibitor, to Pen-2 in a surface plasmon resonance assay.

A surface plasmon resonance (SPR) assay was performed using the Biacore™ 2000 system and control software (Biacore Life Sciences), essentially as described in Warnmark et al. (2001) J. Biol. Chem. 276:23397-23404. Compound 2 or L-685,458 (Sigma #L1790) were diluted 30 fold from a 25 mM stock in 100% DMSO, then each further diluted into running buffer containing 10 mM HEPES, 150 mM NaCl, 1% Triton X-100, pH 7.4. The compounds were run in a 3-fold dilution series over a GST-Pen2 or a free GST flow cell surface. The binding responses at equilibrium for each compound were fit to a 1:1 binding isotherm in order to estimate the binding affinities. Compound 2 was estimated to bind GST-Pen2 with a Kd of 6.5 µM, whereas L-685,458 was estimated to bind with a Kd of 1900 µM.

Example 4

This example shows the characterization of Compound 2 as a gamma-secretase modulator.
   A. Aβ Assays
   The effect of Compound 2 on Aβ levels was determined by three different methods: ELISA, immunoprecipitation and immunoblot analysis, and mass spectrometry analysis.
   1. ELISA Analysis
   For ELISA analysis, CHO-APP$_{Swe}$ cells were seeded at a density of 100K/well in 96-well plates and allowed to adhere overnight. Medium was removed and replaced with complete DMEM medium containing either vehicle alone (DMSO) or a dose-response of Compound 2 or GSI 1 (the gamma-secretase inhibitor designated Inhibitor 1 in Tian et al. (2002) J. Biol. Chem. 277:31499-31505). Cells were incubated with compounds for 18 h, medium collected, and levels of secreted Aβ determined as described below. Cytotoxicity was determined on each well to be less than 30% using an Alamar Blue assay (see US Published Application 2005/0070538).

Secreted Aβ38 peptide was quantified using an ultra-sensitive sandwich ELISA assay kit (Meso Scale Detection catalog #K111FSE-2) and the Meso Scale Sector Imager 6000 for detection, according to the manufacturer's recommended protocol. Captured Aβ was quantified by comparing ECL signals of the samples to a standard curve (included on each plate) using synthetic Aβ prepared in complete DMEM medium. Aβ standard peptides were purchased from Bachem and stored at 0.5 mg/ml in hexafluoroisopropanol (HFIP) at −20° C.

Secreted Aβ40, Aβ42, and total Aβ were measured using specific sandwich ELISAs. Aβ peptides were captured using either an Aβ40-selective monoclonal antibody (B113), an Aβ42-selective monoclonal antibody (A387), or a total Aβ (1-x) capture monoclonal antibody raised to the amino-terminal region (B436) (see PCT publication WO 04/018997).

Briefly, 96-well white ELISA plates were coated with the appropriate capture antibody, wells were blocked with 1% BSA/TBS, and then samples were assayed in complete medium at an appropriate dilution so that the relative luminescent units (RLUs) were in the linear range of the standard curve. Following sample incubation for all ELISAs, plates were washed and exposed to an alkaline phosphatase (AP) conjugated secondary antibody. For Aβ40 and Aβ42, B436-AP was used as the second antibody in the sandwich ELISA. For the total Aβ ELISA, 4G8-biotin (Signet) (a monoclonal antibody that recognizes the Aβ17-24) was used in combination with strepavidin-AP as the detection complex. Thus, for this experiment, total Aβ includes Aβ peptides from 1-x, where x>24. Bound AP-conjugates were detected with CSPD-Sapphire II Luminescence Substrate (Applied Biosystems) and plates were read using a standard 96-well luminometer.

Captured Aβ was quantified by comparing RLU values of the samples to a standard curve (included on each plate) using synthetic Aβ prepared in complete media. Aβ standard peptides were purchased from Bachem and stored at 0.5 mg/ml in hexafluoroisopropanol (HFIP) at −20° C.

Compound 2 produced a concentration dependent decrease of Aβ40 and Aβ42, but did not significantly change total Aβ and markedly increased Aβ38. This is in contrast to the profile of GSI 1, which, in a concentration dependent manner, decreased all forms of Aβ measured.

2. Immunoprecipitation and Immunoblot Analysis

For this analysis, CHO-APP$_{Swe}$ cells were treated with concentrations of Compound 2 ranging from 0.3 nM to 1000 nM, or with concentrations of a gamma-secretase inhibitor, GSI 1 (Tian et al. (2002) J. Biol. Chem. 277 (35), 31499-31505) ranging from 3 nM to 1000 nM, or with vehicle (0.12% DMSO), for 18 hours. The conditioned medium was collected and immunoprecipitated with the anti-Aβ1-12 antibody B436. Samples were denatured and electrophoresed on gels prepared according to Wiltfang et al. (1997) Electrophoresis 18:527-532, with the following improvements: the separating gel contained 12.5% instead of 15% acrylamide, the comb gel layer was omitted, and glycerol (25%) and DTT (100 mM) were substituted for sucrose and β-mercaptoethanol in the 2× sample buffer. Chemically synthesized Aβ$_{1-37}$, Aβ$_{1-38}$, Aβ$_{1-40}$ and Aβ$_{1-42}$ peptides (Bachem) were run as size standards. After electrophoresis, the peptides were transferred to nitrocellulose filters and immunoblotted with a biotinylated B436 antibody to detect the various Aβ alloforms.

Compound 2 treatment was observed to increase the level of Aβ$_{1-37}$ and Aβ$_{1-38}$ present in CHO-APP$_{Swe}$ conditioned medium in a concentration dependent fashion, and lower the level of Aβ$_{1-40}$. In contrast, the gamma-secretase inhibitor, GSI 1, lowered Aβ$_{1-37}$, Aβ$_{1-38}$, Aβ$_{1-40}$ and Aβ$_{1-42}$ levels.

3. Mass Spectrometry Analysis

CHO-APP$_{Swe}$ cells were plated at 1 million cells per well in 6-well dishes and treated with complete DMEM medium containing either vehicle alone (DMSO), 1 μM Compound 2, or 1 μM GSI 1. Cells were incubated for 18 h, medium collected, and levels of secreted Aβ determined by mass spectrometry. Briefly, collected medium was immunoprecipitated overnight using antibody B436 coupled directly to Sepharose. Fifty ng of Aβ1-28 peptide was spiked into the medium as an internal standard. The Sepharose beads were then washed with TBS and bound Aβ was eluted with acetonitrile/0.1% trifluoroacetic acid. Eluate (3-6 μl) was spotted on NP20 chips (Ciphergen). Once the samples were dry, 20% CHCA matrix was spotted (1 μl) and allowed to dry. Chips were read on a SELDI Ciphergen mass spectrometer and Aβ peptides were identified by expected mass and comparison to standard purchased Aβ peptides (Bachem).

Analysis of Aβ peptides by mass spectrometry showed that both Aβ37 and Aβ38, and to a lesser extent Aβ33 and Aβ34, were increased in Compound 2 treated cells compared to vehicle treated cells. In contrast, all Aβ peptide forms were decreased in GSI 1 treated cells compared to vehicle treated cells.

B. Epsilon Cleavage Assay

The effect of Compound 2 treatment on ε-cleavage of a gamma-secretase substrate, Notch, was assessed using an HEK293 clonal cell line overexpressing APP751 and the Notch construct NΔE/S2. The NΔE/S2 construct lacks most of the extracellular domain of Notch (Schroeter et al. (1998) Nature 393:382-386), and when cleaved by γ-secretase results in production of the Notch intracellular domain (NICD). The cells were plated in replicate 24-well dishes and treated in triplicate with 30 μM of Compound 2, 1 μM of the gamma secretase inhibitor N—[N-(3,5-Difluorophenacetyl-L-alanyl)]S-phenylglycine t-butyl ester (DAPT), or vehicle (0.12% DMSO), for 18 h. Following compound treatment, conditioned medium was collected and analyzed for levels of secreted Aβ40, which confirmed compound activity. Cell lysates were prepared and separated on a 4-20% Tris-glycine gel and probed with an anti-NICD antibody (Cell Signaling, #2421) specific for the cleaved NICD, or anti-GAPDH, which served as a loading control for each lane. NICD bands were then quantified by densitometry and an average of replicate values was compared to the vehicle controls.

These data revealed no detectable inhibition of Notch processing up to 30 μM of Compound 2. In contrast, the γ-secretase inhibitor DAPT inhibited NICD formation>95% at 1 μM. Both Compound 2 and DAPT lowered secreted Aβ$_{1-40}$ levels>90% as measured by sandwich ELISA.

To measure γ-secretase-dependent cleavage of E-cadherin, an assay similar to that described by Marambaud et al. (2002) EMBO 21: 1948-1956 was developed. Human A431 cells which endogenously express detectable levels of E-cadherin and cleave full length E-cadherin upon treatment with staurosporine are treated overnight (16-18 h) with either test compound or control γ-secretase inhibitor (DAPT). Cleavage of E-cadherin is induced by a 6 h treatment with 1 μM staurosporine. Cell lysates are analyzed for levels of γ-CTF by western blotting and protein bands are quantified by densitometry. The data show that DAPT completely inhibits the cleavage of E-cadherin, while Compound 2 has no detectable inhibition of E-cadherin processing.

Although the invention has been described with reference to embodiments and examples, it should be understood that various modifications can be made without departing from the spirit of the invention.

All references cited herein are hereby expressly incorporated by reference in their entireties. Where reference is made to a uniform resource locator (URL) or other such identifier or address, it is understood that such identifiers can change and particular information on the internet can be added, removed, or supplemented, but equivalent information can be found by searching the internet. Reference thereto evidences the availability and public dissemination of such information.

That which is claimed is:

1. A screening method for determining whether a test compound has gamma-secretase modulatory activity, said method comprising:
   (1) determining whether said test compound lowers the level of Aβ42 peptide, and
   (2) determining whether said test compound increases the level of Aβ37 and/or Aβ38 peptides, and
   (3) determining whether said test compound has substantially no effect on the processing of other γ-secretase substrates, and
   (4) determining whether said test compound interacts with Pen-2 in an in vitro binding assay;
   wherein only compounds which successfully perform according to each of the above criteria are identified as a gamma-secretase modulator.

2. The method of claim 1 wherein said test compound is further characterized as having less potent effects on lowering Aβ40 peptide relative to effects thereof on Aβ42.

3. The method of claim 1 wherein said test compound has substantially no effect on the processing of Notch, E-cadherin, and/or lipoprotein receptor-related proteins (LRP), and/or the formation of Amyloid precursor protein Intracellular Cytoplasmic/C-terminal Domain, the smaller cleavage product of APP by gamma-secretase (AICD).

4. The method of claim 1 wherein the interaction of said test compound with Pen-2 comprises direct binding thereof to said Pen-2.

5. A screening method for determining whether a test compound that interacts with Pen-2 in an in vitro binding assay has gamma-secretase modulatory activity, said method comprising:
   (1) determining whether said test compound lowers the level of Aβ42 peptide, and
   (2) determining whether said test compound increases the level of Aβ37 and/or Aβ38 peptides, and
   (3) determining whether said test compound has substantially no effect on the processing of other γ-secretase substrates,
   wherein compounds which interact with Pen-2 and successfully perform according to each of the above criteria are identified as a gamma-secretase modulator.

6. A screening method for determining whether a test compound that interacts with Pen-2 in an in vitro binding assay, yet has substantially no effect on the processing of γ-secretase substrates other than Aβ37, Aβ38, Aβ40 and/or Aβ42 peptides, has gamma-secretase modulatory activity, said method comprising:
   (1) determining whether said test compound lowers the level of Aβ42 peptide, and
   (2) determining whether said test compound increases the level of Aβ37 and/or Aβ38 peptides,
   wherein compounds which interact with Pen-2, yet have substantially no effect on the processing of other γ-secretase substrates, and successfully perform according to each of the above criteria are identified as a gamma-secretase modulator.

7. A screening method for determining whether a test compound that lowers the level of Aβ42 peptide, yet has substantially no effect on the processing of γ-secretase substrates other than Aβ37, Aβ38, Aβ40 and/or Aβ42 peptides, has gamma-secretase modulatory activity, said method comprising:
   (1) determining whether said test compound increases the level of Aβ37 and/or Aβ38 peptides, and
   (2) determining whether said test compound interacts with Pen-2 in an in vitro binding assay,
   wherein compounds which successfully perform according to each of the above criteria are identified as a gamma-secretase modulator.

8. A screening method for determining whether a test compound that lowers the level of Aβ42 peptide and interacts with Pen-2 in an in vitro binding assay has gamma-secretase modulatory activity, said method comprising:
   (1) determining whether said test compound increases the level of Aβ37 and/or Aβ38 peptides, and
   (2) determining whether said test compound has substantially no effect on the processing of other γ-secretase substrates, wherein compounds which lower the level of Aβ42 peptide, interact with Pen-2, and successfully perform according to each of the above criteria are identified as a gamma-secretase modulator.

9. A screening method for determining whether a test compound that interacts with Pen-2 in an in vitro binding assay, lowers the level of Aβ42 peptide, and has substantially no effect on the processing of γ-secretase substrates other than Aβ37, Aβ38, Aβ40 and/or Aβ42 peptides, has gamma-secretase modulatory activity, said method comprising determining whether said test compound increases the level of Aβ37 and/or Aβ38 peptides, wherein compounds which successfully perform according to the above criteria are identified as a gamma-secretase modulator.

10. The screening method of claim 1 wherein said gamma-secretase modulator activity has a structure corresponding to Formula (I):

$$(A-L_A)_{0-1}-(B)-L_B-(C)-L_C-(D) \qquad (I)$$

and pharmaceutically acceptable salts, and prodrugs thereof, wherein:

A is optional, and when present is a five or six-membered substituted or unsubstituted cycloalkyl, heterocyclyl, aryl, heteroaryl, cycloalkylene, heterocyclylene, arylene, or heteroarylene;

B is a five or six-membered substituted or unsubstituted cycloalkylene, heterocyclylene, arylene, or heteroarylene; or $B_1$, together with $A_1$, forms a fused ring system;

C is a five or six-membered substituted or unsubstituted arylene or heteroarylene;

D is a five or six-membered substituted or unsubstituted aryl, heteroaryl, arylene, or heteroarylene;

$L_A$ is optional, and when present, is a covalent bond or a linker; and each of $L_B$ and $L_C$ is independently a covalent bond or a linker.

* * * * *

SEQUENCE LISTING

```
<160> NUMBER OF SEQ ID NOS: 1

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```